(12) United States Patent
Webb et al.

(10) Patent No.: US 8,078,270 B2
(45) Date of Patent: Dec. 13, 2011

(54) HEART FAILURE MONITOR QUICKLOOK SUMMARY FOR PATIENT MANAGEMENT SYSTEMS

(75) Inventors: James D. Webb, Maple Grove, MN (US); Tom Dean Bennett, Shoreview, MN (US)

(73) Assignee: Medtronic, inc., Minneapolis, MN (US)

( * ) Notice: Subject to any disclaimer, the term of this patent is extended or adjusted under 35 U.S.C. 154(b) by 0 days.

(21) Appl. No.: 12/897,113

(22) Filed: Oct. 4, 2010

(65) Prior Publication Data

US 2011/0021897 A1    Jan. 27, 2011

Related U.S. Application Data

(62) Division of application No. 10/612,856, filed on Jul. 3, 2003, now Pat. No. 7,831,301, which is a division of application No. 09/809,915, filed on Mar. 16, 2001, now Pat. No. 6,599,250.

(60) Provisional application No. 60/190,272, filed on Mar. 17, 2000.

(51) Int. Cl.
*A61B 5/04* (2006.01)

(52) U.S. Cl. ........................................ 600/513

(58) Field of Classification Search .................. 600/513
See application file for complete search history.

(56) References Cited

U.S. PATENT DOCUMENTS

| | | | |
|---|---|---|---|
| 4,791,931 A | 12/1988 | Slate | |
| 5,330,505 A | 7/1994 | Cohen | |
| 5,368,040 A | 11/1994 | Carney | |
| 5,416,695 A | 5/1995 | Stutman et al. | |
| 5,535,752 A | 7/1996 | Halperin et al. | |
| 5,564,434 A | 10/1996 | Halperin et al. | |
| 5,576,952 A | 11/1996 | Stutman et al. | |
| 5,720,770 A | 2/1998 | Nappholz et al. | |
| 5,752,976 A | 5/1998 | Duffin et al. | |
| 5,951,300 A | 9/1999 | Brown | |
| 6,024,704 A | 2/2000 | Meador et al. | |
| 6,152,885 A | 11/2000 | Taepke | |
| 6,155,267 A | 12/2000 | Nelson | |
| 6,250,309 B1 | 6/2001 | Krichen et al. | |
| 6,264,614 B1 * | 7/2001 | Albert et al. | 600/528 |
| 6,418,346 B1 | 7/2002 | Nelson et al. | |
| 6,440,066 B1 * | 8/2002 | Bardy | 600/300 |
| 6,468,219 B1 | 10/2002 | Njemanze | |
| 7,412,396 B1 * | 8/2008 | Haq | 705/2 |
| 2001/0039504 A1 * | 11/2001 | Linberg et al. | 705/3 |
| 2001/0044588 A1 | 11/2001 | Mault | |

FOREIGN PATENT DOCUMENTS

| | | |
|---|---|---|
| EP | 0710465 | 5/1996 |
| EP | 0779057 | 6/1997 |
| EP | 0796589 | 9/2007 |
| WO | 99/41682 | 8/1999 |
| WO | 99/59460 | 11/1999 |
| WO | 00/30529 | 6/2000 |

* cited by examiner

*Primary Examiner* — George Manuel

(57) ABSTRACT

Continuous remote monitoring of patients based on data obtained from an implantable hemodynamic monitor provides an interactive patient management system. Using network systems, patients are remotely monitored to continuously diagnose and treat heart-failure conditions. A screen displayable summary provides continuous feedback and information to physicians, patients and authorized third parties. The quick look summary includes various sites and presentation tailored to match the patients' and physicians' needs. The quick look summary further includes intelligent features that understand and retain the user's interests, preferences and use patterns. Patients, physicians and other caregivers are seamlessly connected to monitor and serve the chronic needs of heart-failure patients in a reliable and economic manner.

6 Claims, 12 Drawing Sheets

FIG. 5B

| | Hemodynamic Variables | | Patient ID: B007<br>Chronicle Serial Number: 6956 |
|---|---|---|---|

Patient List:

Quick Look
1-Week Trends
Hemodynamic Var.
RV Pressure Waves

Big Pictures
Trends
Triggered Episodes
Daily Minimums List
Daily Minimums Trend
Notes
New Note

Set Up
Load Data
Change Password
QuickLook Options

User Manual

Logoff

Printer Friendly Format

Triggered Episodes:
Tachy: 0    Brady: 0    Patient: 0

| | Selected Transmission | Previous Transmission | Change |
|---|---|---|---|
| Hemodynamic Variables - *Resting values between 12 am and 4am* | | | |
| Heart Rate (bpm) | 69 | 69 | 0 (0.0%) |
| RV Diastolic Pressure (mmHg) | 8 | 11 | -3 (27.3%) |
| RV Systolic Pressure (mmHg) | 38 | 44 | -6 (13.6%) |
| ePAD (mmHg) | 16 | 20 | -4 (20.0%) |
| RV dP/dt$_{max}$ (mmHg/sec) | 226 | 272 | -46 (16.9%) |
| RV Pulse Pressure (mmHg) | 27 | 32 | -5 (15.6%) |
| Summary Criteria<br>Number of Days with Activity of 0 | 3/3 | 18/22 | |

- highlights values out of range

Quick Look Summary
Copyright Medtronic Inc.

Chronicle Monitor    Serial Number: WRK0001033R    Report Generated:

| | Previous Values  view detail | Recent Interrogation  view detail | Change |
|---|---|---|---|
| Volume Status | | | |
| RV diastolic (mmHg) | 6.0 | 5.7 | -.3 (5%) |
| PA diastolic (mmHg) | 18 | 19 | +1 (5%) |
| Automatic Status | | | |
| Resting heart rate (per minute) | 91 | 101 | +10 (12%) |
| +dP/dt$_{max}$ (mmHg/s) | 400 | 410 | +10 (12%) |
| RV Function | | | |
| Pulse Pressure (mmHg) | 32 | 33 | +2% |
| RV Systolic (mmHg) | 38 | 39 | +2% |
| +dP/dt$_{max}$ (mmHg/s) | 400 | 410 | +10 (12%) |
| Activity | | | |
| Average Counts | 2.0 | 1.5 | |

Indicates abnormal value    Note: Although measurements may reflect heart failure status; they may also reflect structural problems, pulmonary vascular resistance, ...

Tachy triggers have been detect since the previous follow-up
No brady triggers have been detected since the previous follow-up Compare recent value to values interrogated on: ▼

Summary Options:

| Thresholds for this patient: | Flag values less than | Flag values greater than | Flag changes greater than |
|---|---|---|---|
| RV diastolic pressure | 2 mmHg | 8 mmHg | 20 % |
| PA diastolic pressure | 12 mmHg | 20 mmHg | 20 % |
| Resting heart rate | 60 per minute | 100 per minute | 10 per minute |
| +dP/dt$_{max}$ | 300 mmHg/s | 450 mmHg/s | 20 % |
| Pulse pressure | 20 mmHg | 40 mmmHg | 20 % |
| RV systolic pressure | 30 mmHg | 40 mmHg | 20 % |
| Activity | ? hours/day | | ? % |

HEART FAILURE MONITOR QUICKLOOK SUMMARY FOR PATIENT MANAGEMENT SYSTEMS

This application is a divisional of U.S. application Ser. No. 10/612,856 filed Jul. 3, 2003, now U.S. Pat. No. 7,831,301, which is a divisional of U.S. application Ser. No. 09/809,915 filed Mar. 16, 2001, now U.S. Pat. No. 6,599,250, which claims the benefit of U.S. provisional application No. 60/190,272, filed Mar. 17, 2000.

FIELD OF THE INVENTION

The present invention relates to implantable hemodynamic monitors (IHMs). Specifically, the invention relates to systems that interface with various hospital monitoring systems to transfer data from the IHMs to doctors and other data processing centers. More specifically, the invention pertains to heart failure data management systems that provide a concise and reliable summary view of information in a manner that is useful for clinicians and health care personnel to monitor, assess, evaluate and treat heart failure conditions in patients. Further, the invention pertains to a system of a bi-directional communication system that is network, Internet, intranet and worldwide web compatible to enable chronic monitoring based on data obtained from the IHMs.

BACKGROUND OF THE INVENTION

The need to monitor, on a frequent and continuous basis, the vital signs associated with hospitalized patients particularly those who are seriously ill is an important aspect of health care. Virtually every hospitalized patient requires periodic measurement in logging of blood pressure, temperature, pulse rate, etc. Such monitoring has typically been performed by having a health care worker periodically visit the bedside of the patient and measuring and/or observing the patient's vital signs using dedicated equipment that is either hooked up to the patient or brought into the patient's room. Such a monitoring procedure is not ideally cost-effective because of its being highly labor intensive.

A great many implantable medical devices (IMDs) for cardiac monitoring and/or therapy whose sensors are located in a blood vessel or heart chamber and coupled to an implantable monitor or therapy delivery device are used for diagnosis and therapy. Such systems include, for example, implantable heart monitors, therapy delivery devices, and drug delivery devices. All these systems include electrodes for sensing and sense amplifiers for recording and/or deriving sense event signals from the intracardiac electrogram (EGM). In current cardiac IMDs that provide a therapy, sensed event signals are used to control the delivery of the therapy in accordance with an operating algorithm. Selected EGM signal segments and sensed event histogram data or the like are stored in an internal RAM for telemetry to be transmitted to an external programmer at a later time. Efforts have also been underway for many years to develop implantable physiologic signal transducers and sensors for temporary or chronic use in a body organ or vessel usable with such IHMs for monitoring a physiologic condition other than, or in addition to, the disease state that is to be controlled by a therapy delivered by the IMD.

A comprehensive listing of implantable therapy devices are disclosed in conjunction with implantable sensors for sensing a wide variety of cardiac physiologic signals in U.S. Pat. No. 5,330,505, incorporated herein in its entirety by this reference.

Typically, an IHM measures blood pressure and temperature signal values which stem from changes in cardiac output that may be caused by cardiac failure, ventricular tachycardia, flutter or fibrillation. These variations may reflect a change in the body's need for oxygenated blood. For example, monitoring of a substantial drop in blood pressure in a heart chamber, particularly the right ventricle, along or in conjunction with an accelerated or chaotic EGM, was proposed as an indicator of a fibrillation or tachycardia sufficient to trigger automatic delivery of defibrillation or cardioversion shock. More recently, it has been proposed to monitor the changes in blood pressure by comparing those values that accompany the normal heart contraction and relaxation to those that occur during high-rate tachycardia, flutter or fibrillation.

A number of cardiac pacing systems and algorithms for processing monitored mean blood pressure or monitored dp/dt have been proposed and in some instances employed clinically for treating bradycardia. Such systems and algorithms are designed to sense and respond to mean or dp/dt changes in blood pressure to change the cardiac pacing rate between an upper and a lower pacing rate limit in order to control cardiac output. Examples of IHMs blood pressure and temperature sensors that derive absolute blood pressure signals and temperature signals are disclosed in commonly assigned U.S. Pat. Nos. 5,368,040, 5,535,752 and 5,564,434, and in U.S. Pat. No. 4,791,931, all incorporated by reference herein.

The Medtronic® Chronicle™ Implantable Hemodynamic Monitor (IHM) disclosed in U.S. Pat. Nos. 6,024,704 and 6,152,885, both incorporated herein by reference in their totality, employ the leads and circuitry disclosed in the above-incorporated commonly assigned U.S. Pat. Nos. 5,535,752 and 5,564,434 patents to record absolute blood pressure values for certain intervals. The recorded data is transmitted to a programmer under the control of a physician in an uplink telemetry transmission from the IHM during a telemetry session initiated by downlink telemetry transmission from the programmer's radio frequency (RF) head and receipt of an integration command by the IHM. Thus, in accordance to the '704 and '885 patents, a method is disclosed in which an IHM is used for deriving reference and absolute pressure signal values using implantable physiologic sensors to detect relative cardiac pressure signal values for storage and transmission.

Further, in accordance with the '704 and '885 patents, calibration of the reference pressure and/or temperature sensors in relation to an external calibrated barometric pressure and/or body temperature sensors could be accomplished. In addition, the same system may be used to interlace digital signal values related to pulmonary artery diastolic pressures with the primary cardiac pressure signal values derived from the right ventricle as disclosed in U.S. Pat. No. 6,155,267, incorporated herein by reference.

Heart failure is a progressive disease. While treatment slows the progression of the disease, current technology does not provide a cure. The best treatment regimen available to date is a combination of continuous diagnosis and drug therapy. Once a heart failure patient is in the hospital, current technology does not provide a continuous means of monitoring the patient during their stay in the hospital. Current practice is based on a dedicated programmer that is used to gain access to the pressure waveforms. Only trained physicians can currently uplink the data, and this is available only when such a trained physician is present, and is therefore not available on a continuous basis.

The present invention enables continuous remote monitoring of patients. In sharp contrast, prior heart failure management involves taking measurements of a few variables in the clinic with accurate catheterization pressures taken only occasionally because of the difficulty of obtaining them.

Accordingly, there is a need to provide continuous and reliable measurements over sustained long period of time. Further, emerging trends in health care including remote patient management systems require that the IMD/IHM be compatible with communication systems, including the Internet, the worldwide web, and similar systems to provide real-time communications and data exchange between the IHM in a patient and a remote center where physicians and other experts reside.

SUMMARY OF THE INVENTION

The present invention relates to chronic data management for cardiac systems. Specifically, the invention pertains to IHMs that monitor heart failure. In its broader aspect, the invention relates to patient management that enables the collection of chronic data for remote patient management, including remote delivery of clinical diagnosis and therapy.

Yet another aspect of the invention includes a user-friendly screen-displayable data management system that presents clinically relevant measurements. Another aspect of the invention provides a software system that enables the translation and transposition of IHM collected data to be presented to a clinician in a manner to enable efficient and reliable evaluation of patient conditions remotely.

The invention further relates to data reduction in a monitoring system as generally disclosed in co-pending application entitled "Implantable Medical Devices Monitoring Method and System Regarding Same" filed on Dec. 15, 1999, U.S. application Ser. No. 09/992,978, incorporated herein by reference in its entirety.

The present invention, inter alia, enables the transfer of a patient's medical data to one or more monitoring stations staffed by expert personnel to have access to the data in real time. Although the IHM device implemented in the present invention relates to the measurement of cardiac pressure, other IHM devices that detect and transmit additional physiological signals such as oxygen saturation, pulmonary artery diastolic and systolic pressure, temperature and related data may be used as the originating device or data source. Transferring real-time signals from IHMs to various physician portals and locations provides a highly accentuated medical service and effective chronic monitoring of patients.

In one aspect of the present invention an IHM device determines the hemodynamic status of a patient from measurement of pulmonary pressure and right atrial pressure obtained from a single absolute pressure sensor implanted in the right ventricle. Both of these values have been shown to correlate to the degree and extent of cardiac failure of a patient. The IHM continually monitors the right ventricular pressure using an absolute pressure sensor and marks the right ventricular pressure at the moment of specific events.

One aspect of the present invention is to provide a means by which physicians could view data available via real-time telemetry other than using a local data retrieving system, such as a programmer. Currently, physicians use the programmer to view the real-time pressure wave along with the EGM tracing. Using the present invention, the IHM device would be able to telemeter real time signals to a system via a programmer or other instrument to a remote location.

Another aspect of the present invention relates to the presentation of data from IHMs in a summary view that's useful and familiar to clinicians and patients. Yet another aspect of the present invention includes a process by which data is collected by IHMs, which data includes but is not limited to heart rate patient activity and pressure data, to establish that the patient is in a state of repeatable data routine on a daily basis. For example, this might mean application of a magnet when the patient is lying down, or using devices such as time-of-day counters, activity sensors, posture sensors, etc. Such data is retrieved for analysis via home monitors, programmers or similar devices, and the data sent over an Internet/intranet, worldwide web or a similar network to a remote location for analysis by clinicians or for storage and archiving at a Medtronic server.

The data is processed for collection with past pull-up records to compose a continuous patient record. Specifically, clinically relevant measurements are pulled out of the data. This would mean observing the average values measured during a daily test, including, for example, the patient reclining for 5 minutes. These values and the deviation or change are compared against clinical norms and flagged for the user if they are abnormal. For example, color plus footnote designations may be used to identify or flag abnormal data. Other variations such as italics, specialized fonts, bigger fonts, e-mail reports, faxed reports may be used to identify deviations from normal clinical data or established chronological data for the patient. The clinical norms can optionally be modified for each patient by the clinician and then serve as a clinical baseline for the particular patient.

One other aspect of the present invention is the display of data which without limitation, includes the most recent daily test data along with data from the previously interrogated data. A comparative value between the two and a previous interrogation date to compare collected data with chronological data are used.

Yet another aspect of the present invention includes a single page view of chronic heart failure status, translation of raw data into clinical indicators of heart failure status, analysis of changes in indicators over a user-selectable time period, flags and indicators to identify changes that are outside of clinical norms, tailoring of graphical displays and data management to a patient's clinical norms, means to determine if the patient is in a state of repeatable condition from day to day, and automated data analysis triaging which provides a foundation for further data analysis and automation.

BRIEF DESCRIPTION OF THE DRAWINGS

FIG. 5B is a representative hemodynamic variables display screen.

FIGS. 6 & 7 is a quick look summary in accordance with the present invention.

DETAILED DESCRIPTION OF THE PREFERRED EMBODIMENT

Figure 1A:
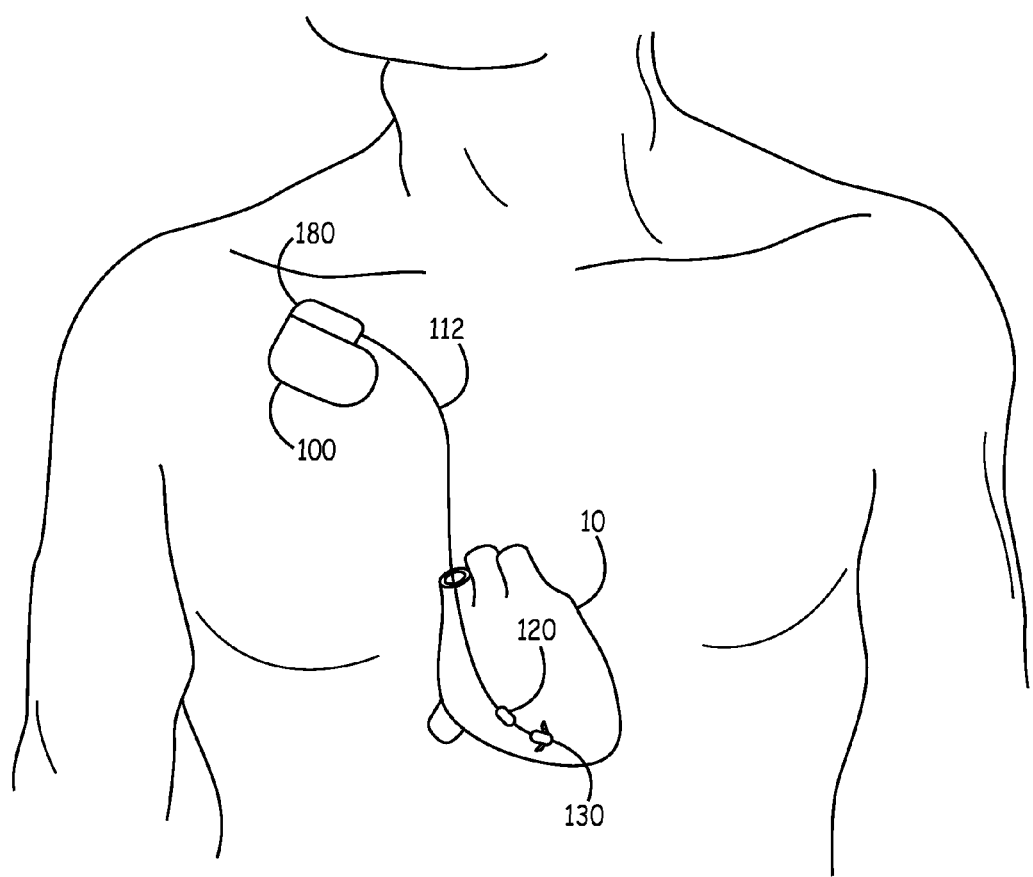
FIG. 1A shows a diagram illustrating an implantable medical device that incorporates an absolute cardiac blood pressure sensor and an IHM device in accordance with the present invention.

FIG. 1A represents a patient with implanted medical device incorporating an absolute cardiac blood pressure sensor such as the IHM discussed hereinabove. Specifically, IHM/IMD 100 is coupled to an absolute cardiac blood pressure sensor 120 in a patient's heart 10 for recording absolute blood pressure values. IMD 100 is depicted implanted subcutaneously in the patient's chest region and it is coupled at its connector module 180 to a lead 112 extending through blood vessels into the right ventricle of the patient's heart 10. The blood pressure sensor 120 is located on lead 112 just proximal to the lead's distal tip 130 for passively fixing it in position to accommodate continuous movement of the heart 10. In this structure lead 112 and blood pressure sensor 120 correspond to those disclosed in detail in the above-incorporated commonly assigned '434 and '752 patents for deriving absolute blood pressure. The IMD 100 that monitors the physiological condition or state is programmable and/or can be interrogated by an external instrument such as a programmer through the use of bi-directional or RF telemetry that exchanges data and commands via uplink and downlink RF telemetry transmissions through the patient's skin.

In the context of an implantable blood pressure monitor a series of absolute blood pressure signal values are sensed periodically or in response to a signal provided by hospital personnel for example, a telemetry downlink signal to initiate real time data transmission. The absolute blood pressure value signals are continuously transmitted so that physicians, clinicians, nurses or other medical experts can determine the status of the patient's cardiac pressures and associated episodes recorded within the required time of day. The physician uses an external programmer to generate and transmit an interrogation command via a downlink telemetry transmission to the IMD 100. IMD 100 recognizes the command and initiates a continuous uplink telemetry transmission of the absolute pressure data in response. The uplink telemetry continues until the IMD system fails to detect further commands.

Figure 1B:
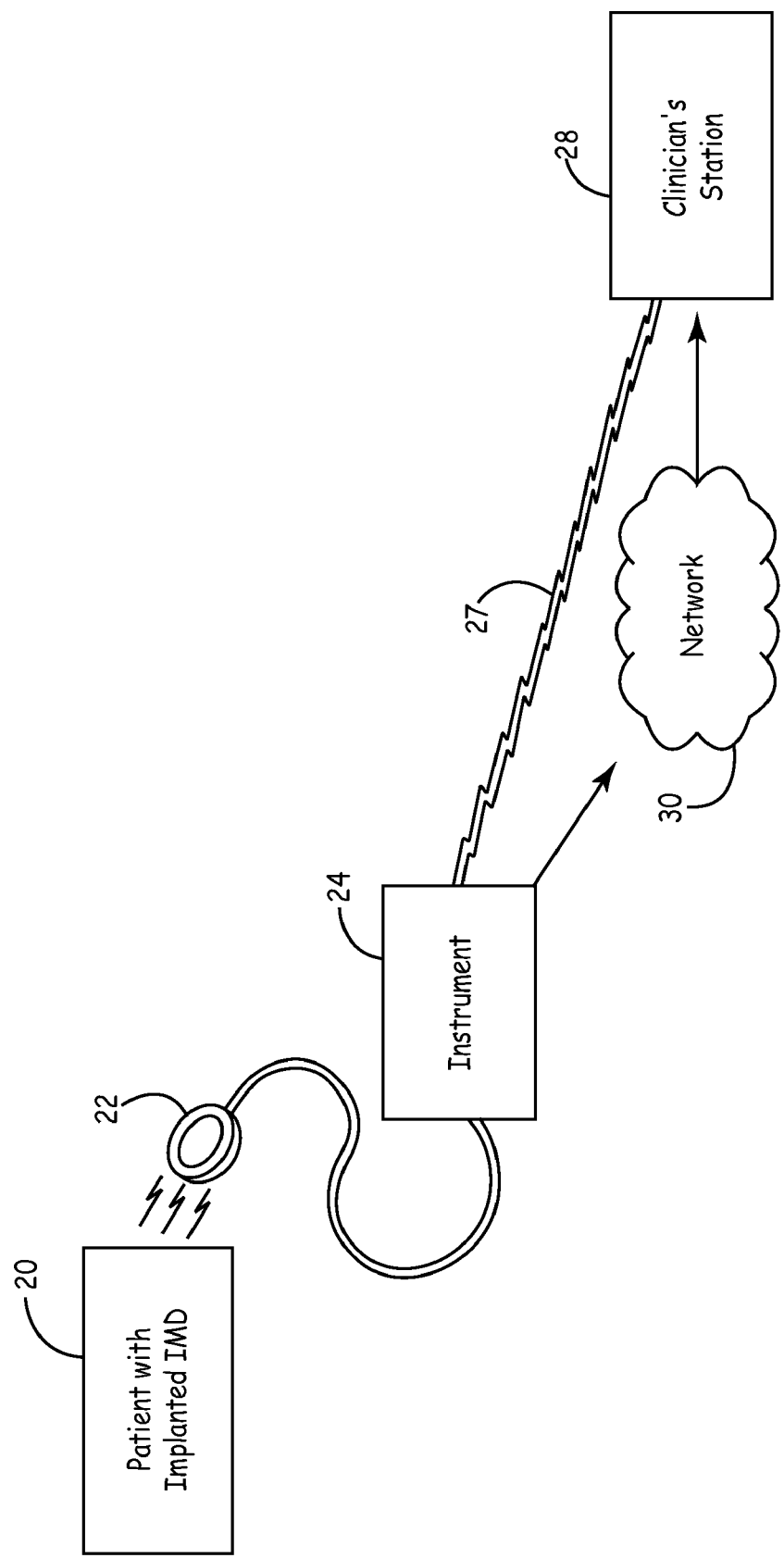
FIG. 1B is a block diagram illustrating various data communication systems from the IMD.
Figure 1C:
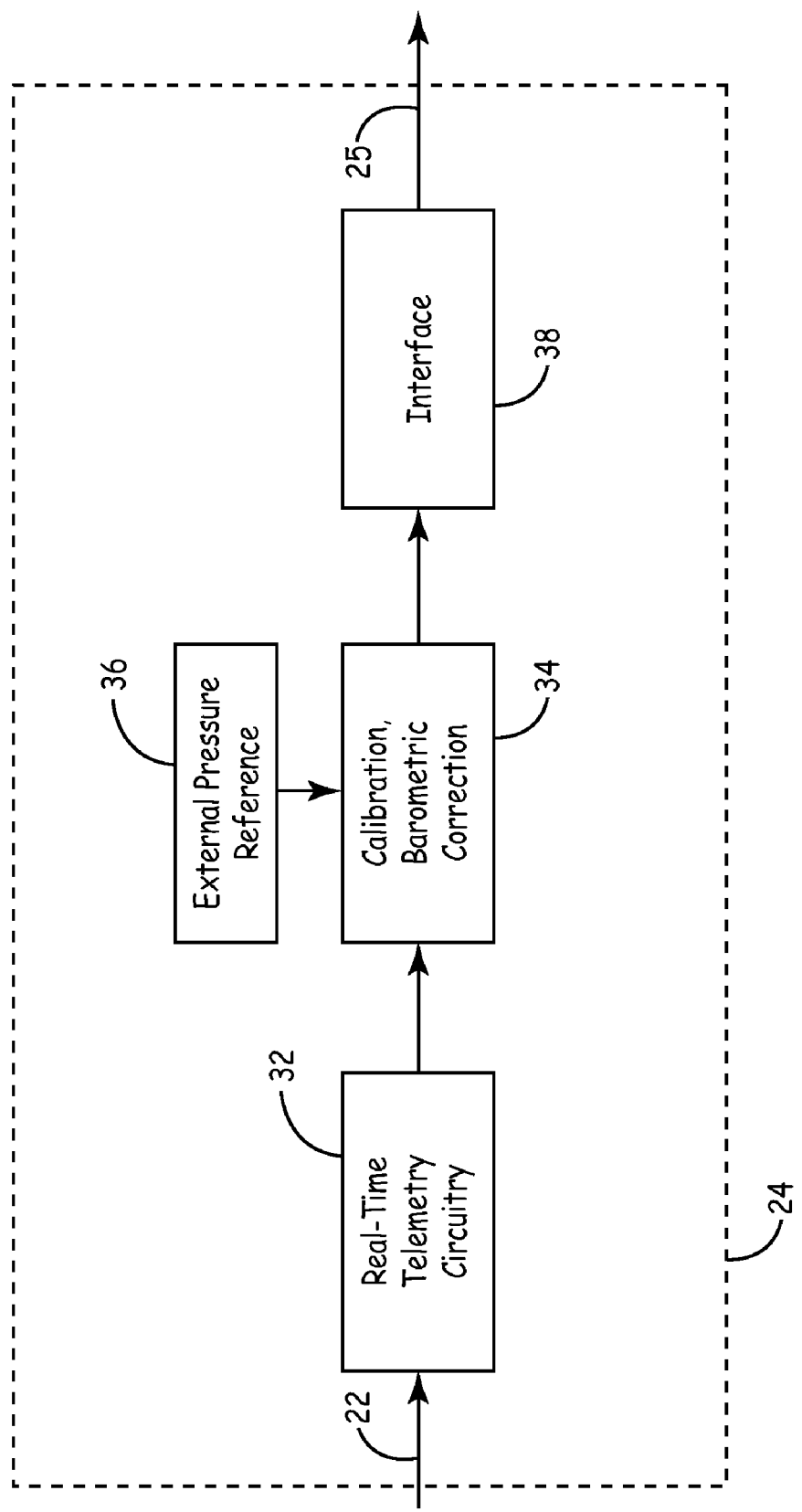
FIG. 1C is a block diagram illustrating signal transmission from the IMD to a remote station.

FIG. 1B illustrates a general scheme by which patient data could be transmitted to a remote clinician's station. The communication scheme enables continuous monitoring of patients either in a hospital setting or in a home environment. Pressure signals are acquired from the IMD via telemetry head 22 or equivalent device and uplinked to instrument 24. Instrument 24 may represent a programmer or an in-home monitor adapted to communicate with IMD 20. Instrument 24 maintains wireless communication 27 to transfer data to clinician's station 28. Alternatively, instrument 24 may be adapted to transfer data via network 30 representing Internet, extranet, worldwide web or a similar network. The data is then transferred to clinician's station via modem, cable or equivalent data transfer system.

Figure 2:
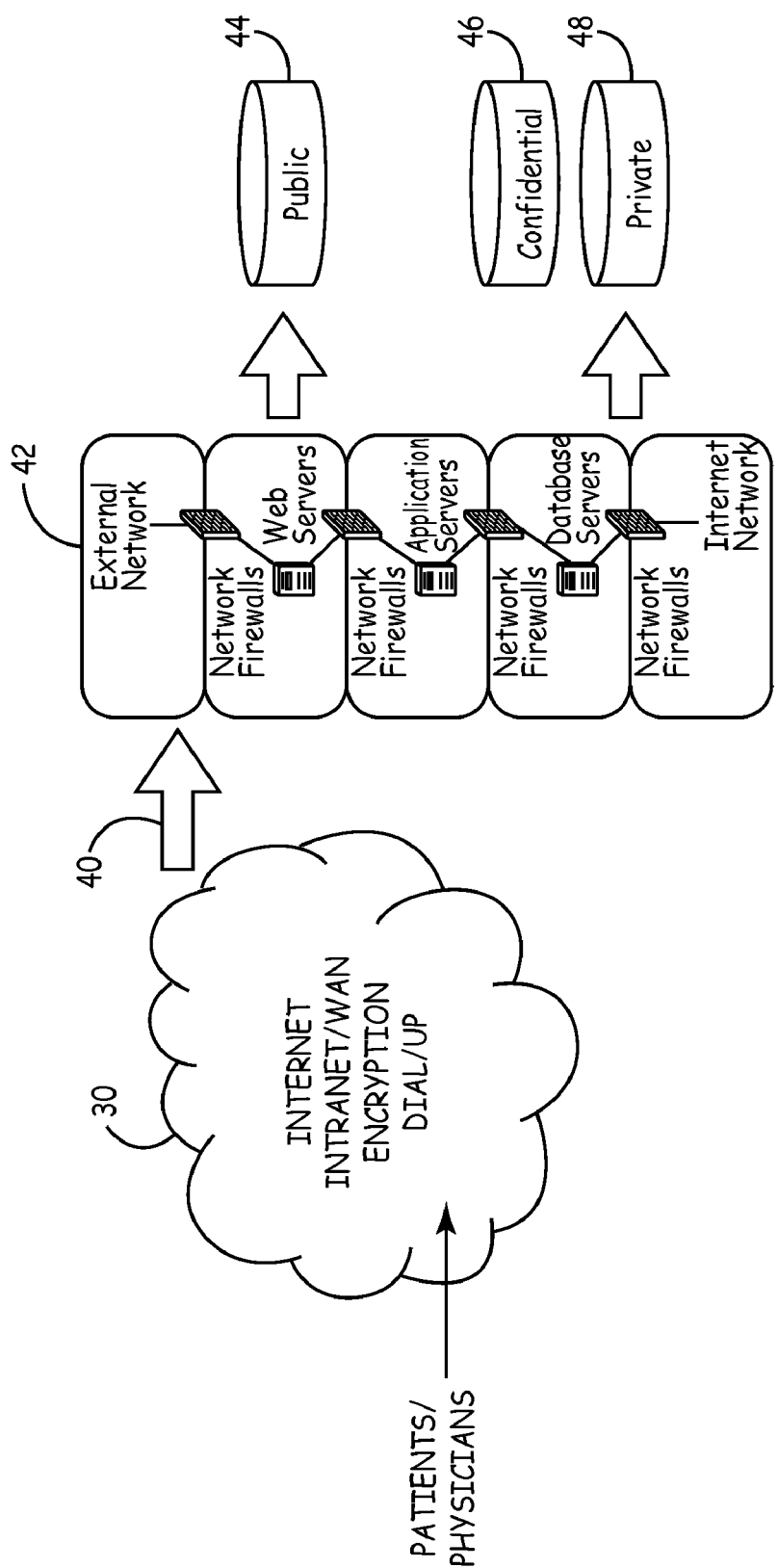
FIG. 2 is a block diagram illustrating the remote communication system within which the present invention is incorporated.

FIG. 2 represents a detailed aspect of network 30 that is accessible to patients and physicians within which search engine 40 enables access to various zones 42, including a dedicated public zone 44, confidential zone 46 and private zone 48. These zones represent various data management centers that are either interconnected or segregated based on privacy and security requirements. For example, public zone 44 is accessible to all patients, physicians and the public to provide general information about medical devices and related medical information and services. In sharp contract, confidential database 46 and private information 48 are accessible to patients and physicians based on strict security and encryption systems for access on a need-to-know basis.

Figure 3:
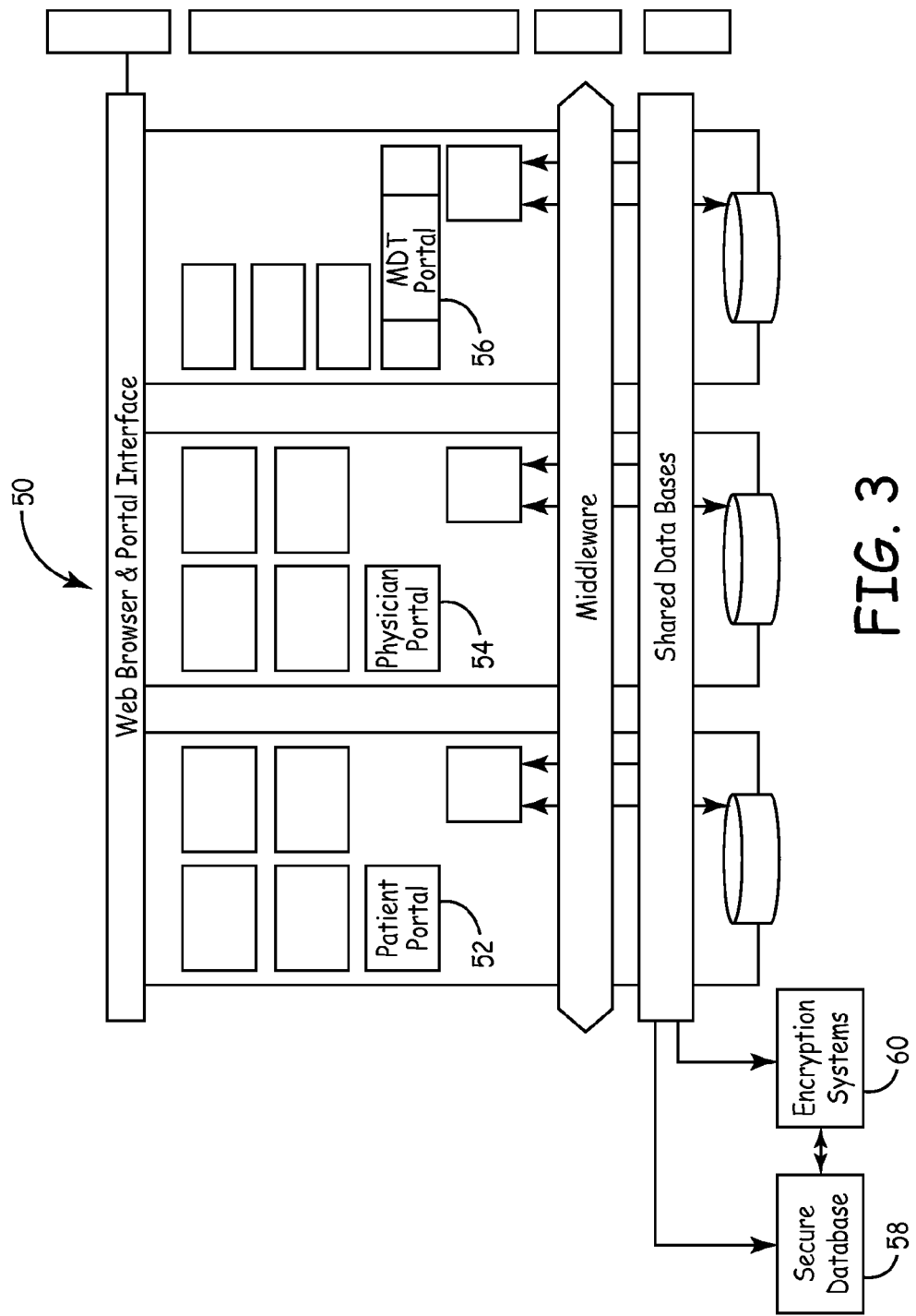
FIG. 3 is a block diagram representing a web browser and portal interface for the present invention.

Referring now to FIG. 3, web browser and portal interface 50 representing patient portal 52, physician portal 54 and Medtronic (MDT) portal 56 are shown. These portals share a common database with additional secure database 58 and encryption system 60 interconnected therewith.

Figure 4A:
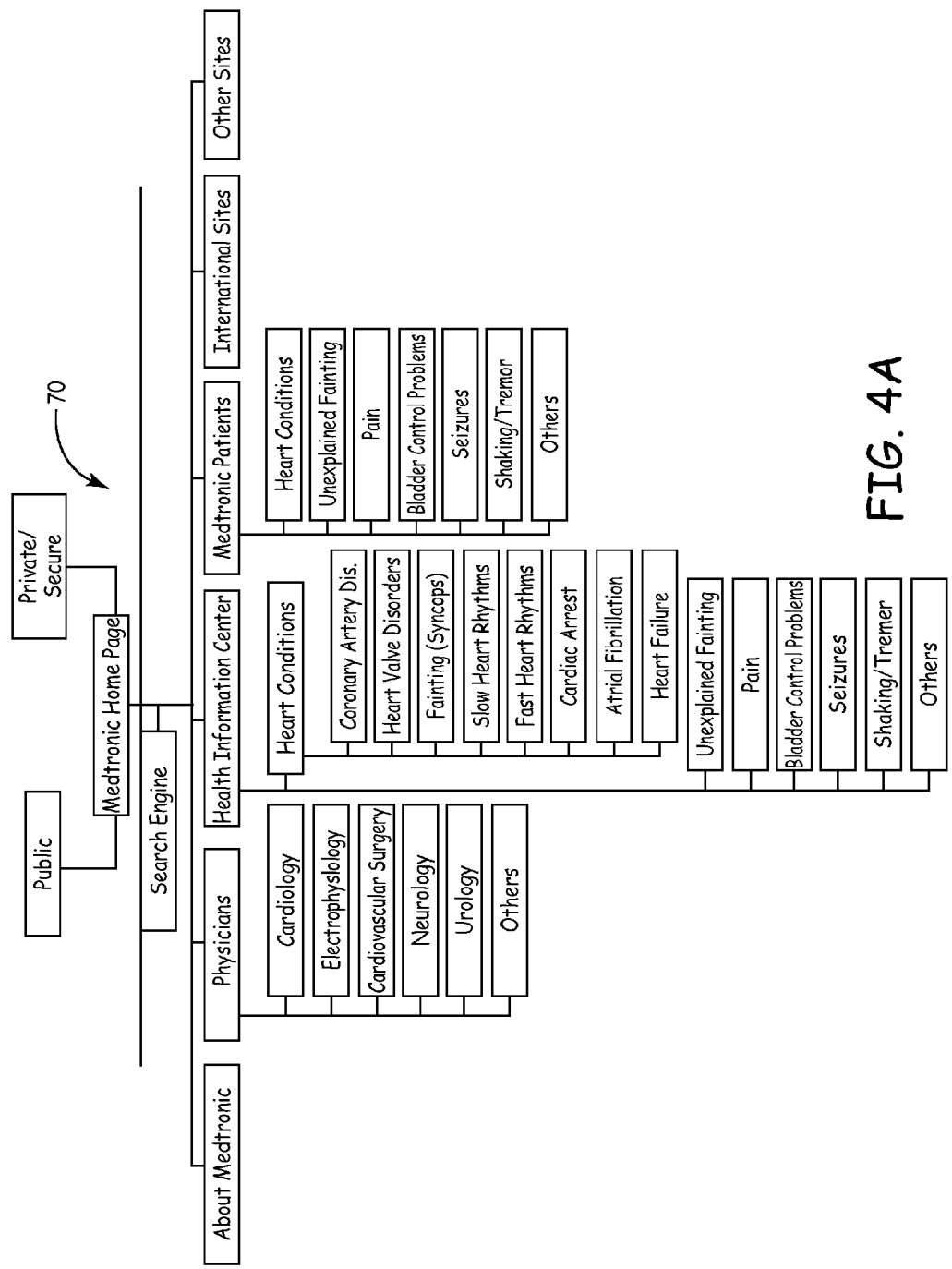
FIG. 4A is a block diagram representation illustrating a Medtronic home page at the Medtronic server in which data may be archived in accordance with the present invention.

FIG. 4A is a general representation of a Medtronic home page 70 in accordance with the present invention. The home page is segregated between public and private/secure pages. Specifically, a physician section, patient section and a general public information section are depicted. The physician's section is highly scalable and operates both on the public and private secure sections. Similarly, the patient section relates to information on various medical devices including related therapy and diagnosis. Further, similar to the physician's site, the patient site includes private/confidential segments.

Figure 4B:
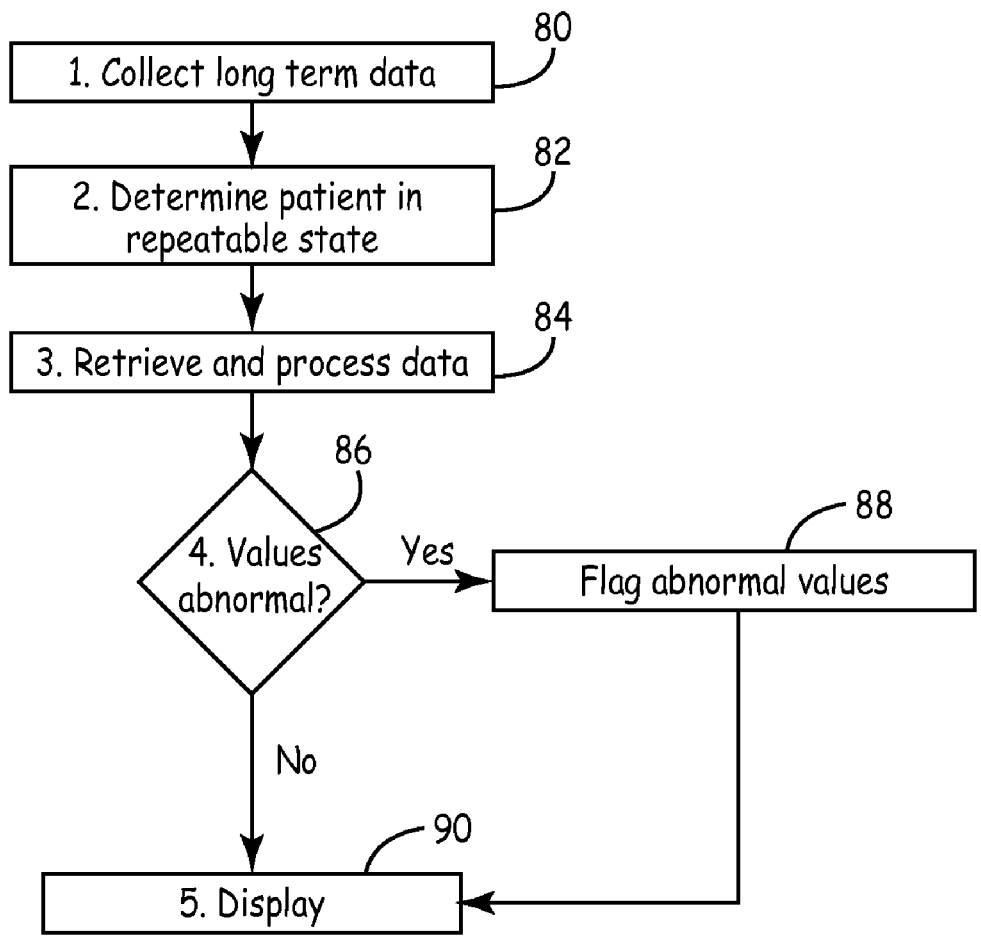
FIG. 4B is a logic flowchart representing high level quick look summary in accordance with the present invention.

FIG. 4B represents a general logic flow diagram for a quick look summary in accordance with the present invention. Specifically, the system is initiated under logic step 80 where long-term data is collected via IMD 100. The long-term data is refined to determine if the patient is in a repeatable state under logic step 82. Subsequently, the data is retrieved and processed under logic step 84. Thereafter, under decision step 86 the values of the processed data are reviewed to see if they are abnormal. If these values prove to be abnormal, they are flagged as abnormal values under logic step 88 and the results are displayed under logic step 90. In the alternate, if the values are found to be normal, they are displayed under logic step 90. One of the significant aspects of the present invention is the presentation of highly user-friendly quick look summary of data collected by IMD/IHM 100 to clinicians, patients and other health providers.

Figure 5A:
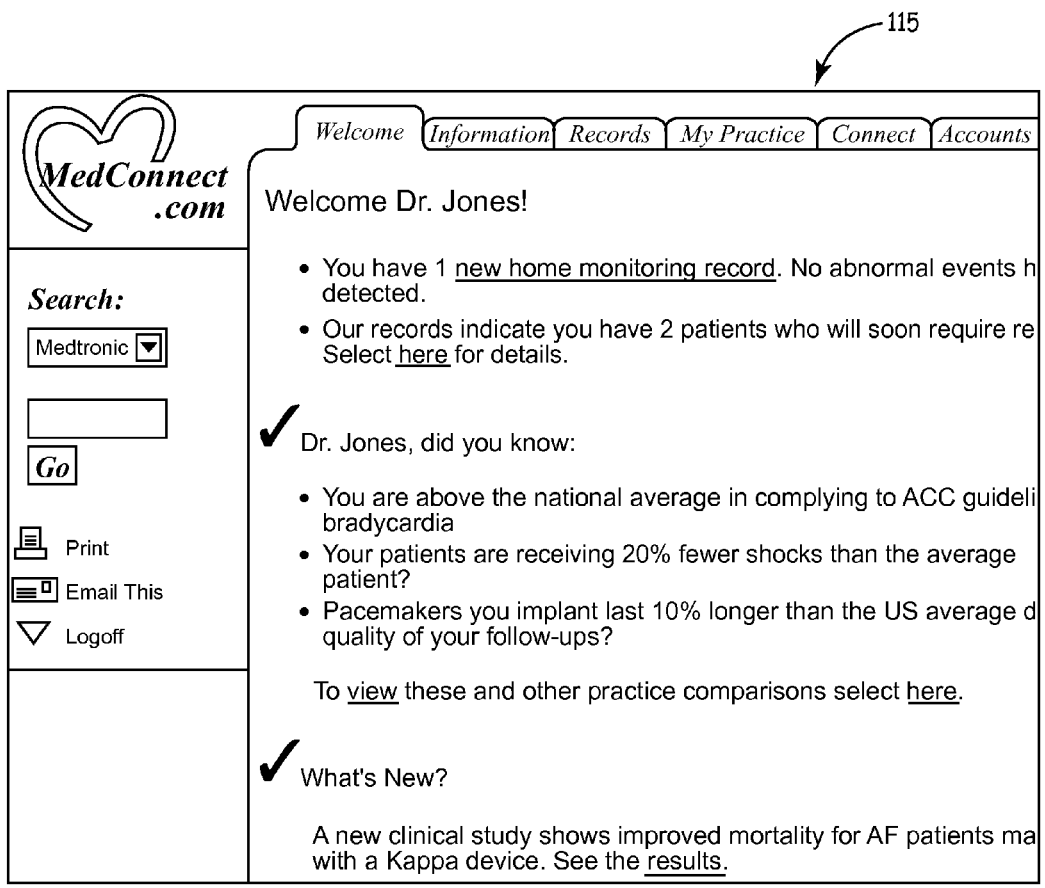
FIG. 5A is a representative sample of a welcome screen.

Referring now to FIG. 5A, a representative screen encountered by a doctor using the Internet site provided in accordance with the present invention is shown. Specifically, the screen includes various tabs, one of which is to welcome the user. The welcome screen identifies the doctor and updates him or her on how many home monitoring records have been reviewed and how many abnormal events have been detected. The doctor is also informed of the number of patients who may require review. The doctor is also given various information regarding his or her practice and is also informed on what is new in the art vis a vis specific devices and medical conditions. The screen is highly interactive and based on past site use behavior of the doctor, the software is able to understand and retain the doctor's interests and highlight unused features.

In the "What is New" section, for instance, the screen interactively provides the doctor with the latest information regarding clinical studies including the devices that are released in the user's countries. The "Links" section provides links to related medical sites. The list of links is maintained by Medtronic, so only approved sites will appear. The list of potential links is narrowed by the user's areas of interest. Clinicians can also provide recommended links to their patients. This will appear in the patient portal and are customized by the recommended links, the type of devices the patient has implanted, the local language to be used and a track record of previous links that have been used.

Further, patient records of device and recorded data will be available for viewing and entry. This data may have been collected by home monitors, programmers, extenders, registration database or imported from clinic databases. Users can arrange the view of records, listable to their liking by date, name, ID and status. Specifically, status indicators are used for home monitoring data yet to be viewed or with errors. The records may include in-office follow-up test results, interrogated diagnostic data settings and measurements, data imported from pacing databases such as EKG indication, medications including control of compliance, monitoring functions, key physiologic data such as indications for implant, links to other online components of a patient's chart such as lab results, notes entered, data integrated across patient sessions such as episode logs and trends, patient demographics and patient diary entries.

The system may also be customized based on whether the portal is used to store in-home or programmer records for the particular patient. All parts of the patient's records that are attributable to the patient are clearly patient private data. Encryption and adequate authentication must be used for access. Attribution of who enters and edits changes is also supported by the system software.

Appointment scheduling provides an automatic means for scheduling home-monitoring sessions so home monitoring could be conducted without additional burden on the clinic scheduling staff. Physicians may enter their prescribed follow-up intervals and then the system can schedule the follow-up days. Patients can customize their schedule without the help of the clinical staff. The scheduling may also integrate with the clinic's in-office scheduling enabling doctor appointments to be made online.

Accounts billing are automated. Automation of the filling out of billing statements is also provided. Medical device follow-up regiments can often automatically be determined from session data. The data is forwarded to the clinician's billing system or a third party billing clearing house. Medtronic device registration forms will be web-enabled. Direct entry on the web or import from un-tethered data entry applications will be supported. Entry on the web will enable access by customers rather than field representatives without the high distribution and support cost encountered today with PC applications.

Clinical study content will be available to clinical study investigators. This could include entry of clinical data forms, discussion groups, newsletter and results reports. The site is customized based on which studies the user is a part of and the local language used. Physicians can compare their practice by comparing their practice data to data aggregated from other practices and practice guidelines. Specific comparison and points can be offered with custom filters. Eventually data mining may be offered. This will include and expand on the current capabilities of the CV views extranet applications. This part of the site could be customized based on collected user's data that is also made available for comparisons. Further, information about the user's practice to derive comparison definitions, for example with other practitioners in the area of expertise may be provided.

The site also includes reports for tracking product performance and will maintain tags on the referring physician. The distribution of reports is greatly enhanced through web-enabled features. Specifically, the content is tailored to each practice. For example, product performance can be incorporated with web devices such as a palm device which may be on the person of the patient or the physician. Similarly, the accuracy of reports can be enhanced by joining data. For example, closer monitoring reports may contain more accurate battery projections derived from follow-up and continuous monitoring of actual device data.

The system enables remote viewing. Specifically, users can remotely view patient stations through instruments connected to the Internet 30. Sessions with programmers, extenders, acute monitors and home monitors will be viewed through web browsers or a PC. Users will have access to a switchboard of available instruments they have rights to connect to and access the contents thereof. The connection is supported in any order whether it is browser or instrument first. Preferably, the site is customized by identifying which instruments the user has access rights to. Rights are assigned to physicians and clinical personnel as needed.

In the same manner, the link for patient portal 52 is a secure website for patients already implanted with Medtronic devices and their families. It includes the web content that requires secure access not available in the Medtronic public website 56. Patient portal 52 provides personalization, automatically providing only the information pertinent to the patient's device and disease. This is combined with a consistent user interface for the diverse applications being provided for a highly distributed user-friendly web experience.

Welcome screen 155 of FIG. 5A highlights important information with more detailed features. The site is customized by patient's names, what devices the patient has implanted, marketing preferences of what news or new products are of interest, physician control of what the patient has access to, past portal use to understand interests and highlight unused features, and what local language the patient uses.

One of the significant aspects of this site includes a home monitoring section which closes the loop for home-monitored patients. These patients can view whether sessions were successful or trouble-shoot errors. They can gain reassurance by viewing high-level results. Clearly this will reduce the burden of phone calls on clinicians. The site is customized by results of home monitoring sessions. The type of implanted device and home monitor that are proper to a patient are generally decisions made by the patient's physician. For security reasons home-monitoring results may be considered patient private data and will require encryption and user authentication. The site also provides appointment scheduling in which an automated means for scheduling home-monitoring sessions is implemented without additional burden on clinic scheduling staff. Physicians can enter their prescribed follow-up intervals and the system is intelligent to schedule the follow-up days. Patients can customize their schedule without the help of the clinical staff. The scheduling may also integrate with a clinic's in-office scheduling enabling doctor appointments to be made online.

Patient portal 52 also includes a diary section where daily medical journal entries can be captured. Voice or text can be captured either on the diary screen or potentially on a home monitor. Regardless of where it is entered, the diary screens would provide options to review and edit the contents of a diary. By putting the diary online, it is instantly available to all medical caregivers. Further, the diary does not need transcription or transfers to become part of a medical chart because of automatic entry.

Yet another significant aspect of the screen display at patient portal 52 includes the management of patient ID cards. Requests for replacements and validation of patient's information is automated on patient portal 52. Patients can also print out replacement ID cards for use while the processing of a permanent card is in progress. Patient portal 52 also enables patients to control the rights to their records. Specifically, patients will have rights to grant control and access rights to their records as they may deem necessary.

Referring to FIG. 5B, a quick look summary of hemodynamic variables 125 is represented. The screen provides one-week trends for hemodynamic variables RV pressure waves.

For example, triggered episodes could be selected under a tachy-, brady- or patient-triggered events. A tachy-triggered event, for example, would inform the user if the patient has tachy-triggered events. Similarly, a brady-triggered event informs the user if the patient has brady-triggered events. Further, patient-triggered events relate to information indicating patient-triggered events.

Referring to FIG. 6, quick look summary screen 140 represents various parameters useful to determine a tachy or brady trigger. A tachy-trigger notification informs the user if the patient has tachy-triggered events. If there are tachy-triggered events the device information network for example, IHM 100, will notify the designated person, for instance a nurse, doctor or health provider electronically that events have occurred by e-mail, pager or other means. Similarly, a brady-triggered notification would be dispatched in the event there are brady-triggered events. IHM 100 will notify the designated person about the event. Patient-triggered notification is also dispatched in the same manner.

Referring to FIG. 7, under display screen 150, the software system enables analysis of comparative values based on a comparison of recent values to values interrogated on a prior time period. Patient portal 52 and physician portal 54 provide various ways of presenting clinical information. Specifically, daily minimums of heart rate for quick look, RV systolic pressure, daily minimums of RV diastolic pressure, daily minimums of estimated pulmonary artery pressure, daily minimums of RV pulse pressure, daily minimums of RV dp/dt, highlighting out-of-range heart rate, highlighting out-of-range RV systolic pressure, highlighting out-of-range RV diastolic pressure, highlighting out-of-range ePAD pressure, highlighting out-of-range RV pulse pressure, highlighting out-of-range RV dp/dt, notification of heart rate out-of-range, notification of RV systolic pressure out-of range, notification of RV diastolic pressure, notification of ePAD pressure, notification of RV pulse pressure, notification of RV dp/dt out-of-range, highlighting changes in heart rate. Specifically, the quick look will determine and report changes in heart rate which have occurred in a patient between the daily minimum values contained in the file selected for examination and the daily minimum values from a previous file. More specifically, values are compared to determine if the differences lie outside a user-defined threshold is defined in the quick look setup and can be tailored on a patient-by-patient basis. This feature allows the user to define differences either based on actual values or percentages. Highlighting changes in RV systolic pressure relates to pressures which have occurred in a patient between the daily minimum values contained in the file selected for examination and the daily minimum values from a previous file.

Highlighting changes in RV diastolic pressure enables the quick look to determine and report changes in RV diastolic pressure which have occurred in a patient between the daily minimum values contained in the file selected for examination and the daily minimum values from a previous file. Similarly, the quick look will determine and report changes in RV pulse pressure which have occurred in a patient between the daily minimum values contained in the file selected for examination and the daily minimum values from a previous file. Highlighting changes in RV dp/dt includes determination and reporting of changes in RV dp/dt which have occurred in the patient between the daily minimum values contained in the file selected for examination and the daily minimum values from a previous file. Notification of large heart rate change is implemented by enabling IHM 100 information network to notify a designated person electronically that changes in heart rate greater than set targets have occurred. A notification may be sent by e-mail, pager and an equivalent medium.

Similar notification of large RV systolic pressure changes, large RV diastolic pressure changes, large ePAD pressure changes, large RV pulse pressure change, and RV dp/dt changes may be made. The quick look allows the user to select from a list of previous files. A specific file may be selected for data against which the current file is compared to determine if hemodynamic values have changed. Accordingly, quick look compares the daily minimum values from the selected file set of previous files to show the user variation that may have occurred. Additionally, while the quick look page allows the user to examine a selected file, its comparison to threshold values and comparison to a previous file, it also provides the daily minimum plots to enable the user to see a time/trend plot of all daily minimum values for all variables. Further, a daily minimum list may be used to examine a selected file, its comparison to threshold values and its comparison to a previous file to see a listing of all daily minimum values for all variables.

Figure 8:
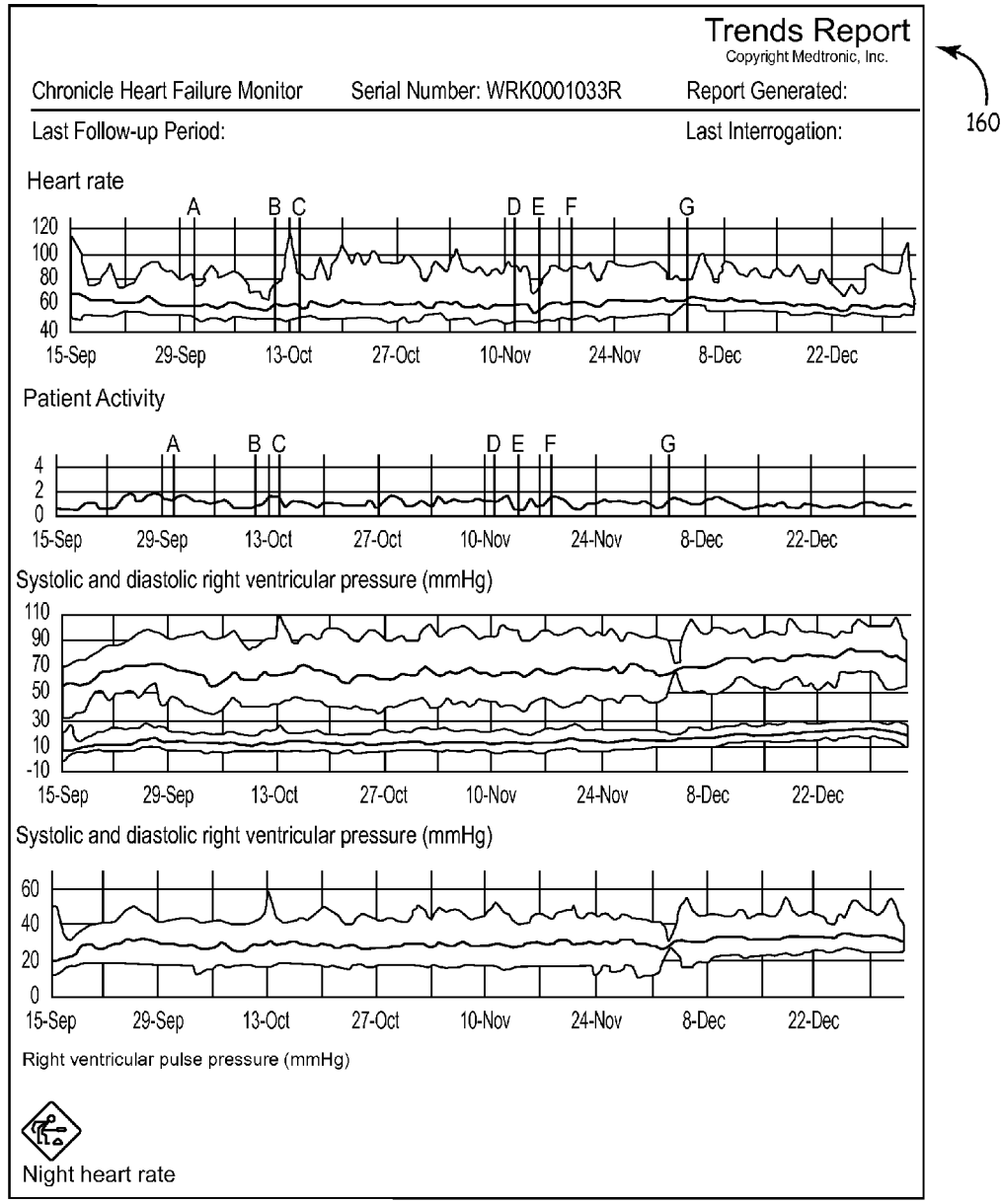
FIG. 8 is a representative screen for a trends report.
Figure 9:
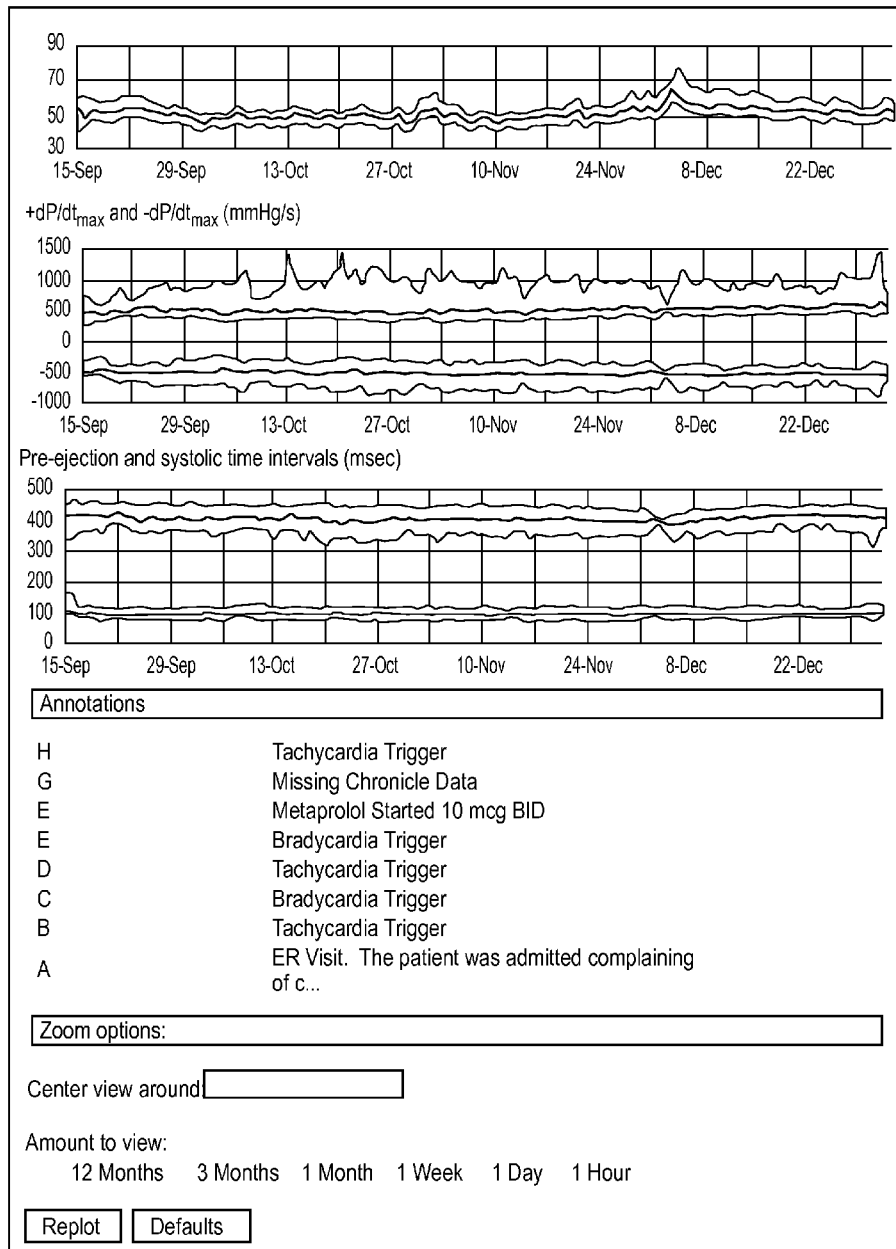
FIG. 9 is a representative screen for a trends report similar to FIG. 8.

Referring now to FIGS. 8 and 9, trends report 160 and 170 are represented. Specifically, heart rate, patient activity, systolic and diastolic pressures and similar cardiac/physiologic parameters collected over a period of several weeks. Trend reports for night heart rate, +dp/dt and −dp/dt including pre-ejection systolic time intervals may be displayed. Trend directions for 12 months to 1 hour may be selected for review.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. A heart failure monitor including a quick look summary implemented in a network having a web browser and portal interfaces to transfer and manage data from the heart failure monitor, the web browser and portal interfaces comprising:
   a patient portal;
   a physician portal; and
   a device manufacturer portal;
   said patient, physician and device manufacturer portals having shared databases and further including secure databases and encryption systems in data communications thereof.

2. The interface of claim 1 wherein said patient portal includes a quick look summary tailored to the patient.

3. The interface of claim 2 wherein said quick look summary included in said patient portal is customizable for various patient preferences.

4. The interface of claim 1 wherein said physician portal includes a quick look summary tailored to the physician.

5. The interface of claim 1 wherein said quick look summary is customizable for various physician preferences.

6. The interface of claim 1 wherein the data includes at least a one of the following: an internal cardiac pressure value, an oxygen saturation value, a pulmonary artery diastolic pressure, a pulmonary artery systolic pressure, a cardiac-blood temperature value, a right atrial pressure value.

* * * * *